United States Patent
Spriewald et al.

(10) Patent No.: US 10,618,871 B2
(45) Date of Patent: Apr. 14, 2020

(54) PROCESS FOR PRODUCING ISOCYANATE AND AT LEAST ONE FURTHER CHEMICAL PRODUCT IN AN INTEGRATED PRODUCTION

(71) Applicant: Covestro Deutschland AG, Leverkusen (DE)

(72) Inventors: Jürgen Spriewald, Kölln-Reisiek (DE); Richard Adamson, Leichlingen (DE); Thomas Knauf, Dormagen (DE)

(73) Assignee: Covestro Deutschland AG, Leverkusen (DE)

( * ) Notice: Subject to any disclaimer, the term of this patent is extended or adjusted under 35 U.S.C. 154(b) by 0 days.

(21) Appl. No.: 16/325,809

(22) PCT Filed: Aug. 15, 2017

(86) PCT No.: PCT/EP2017/070675
§ 371 (c)(1),
(2) Date: Feb. 15, 2019

(87) PCT Pub. No.: WO2018/033536
PCT Pub. Date: Feb. 22, 2018

(65) Prior Publication Data
US 2019/0185419 A1  Jun. 20, 2019

(30) Foreign Application Priority Data

Aug. 17, 2016  (EP) ..................... 16184618
Jun. 30, 2017  (EP) ..................... 17178902

(51) Int. Cl.
| | | |
|---|---|---|
| C07C 263/10 | (2006.01) | |
| C07C 209/54 | (2006.01) | |
| C07C 209/78 | (2006.01) | |
| B01D 1/26 | (2006.01) | |
| B01D 3/14 | (2006.01) | |
| C07C 211/50 | (2006.01) | |
| C07C 265/12 | (2006.01) | |
| C07C 265/14 | (2006.01) | |

(52) U.S. Cl.
CPC .............. C07C 263/10 (2013.01); B01D 1/26 (2013.01); B01D 3/148 (2013.01); C07C 209/54 (2013.01); C07C 209/78 (2013.01); C07C 211/50 (2013.01); C07C 265/12 (2013.01); C07C 265/14 (2013.01)

(58) Field of Classification Search
CPC ... C07C 211/50; C07C 209/54; C07C 209/78; C07C 263/10; C07C 265/14; C07C 265/12; B01D 1/26; B01D 3/148
See application file for complete search history.

(56) References Cited

U.S. PATENT DOCUMENTS

| | | |
|---|---|---|
| 2,256,999 A | 9/1941 | Castner |
| 4,265,834 A | 5/1981 | Birkenstock et al. |
| 4,772,757 A | 9/1988 | Lailach et al. |
| 4,847,408 A | 7/1989 | Frosch et al. |
| 4,851,570 A | 7/1989 | Zaby et al. |
| 5,053,539 A | 10/1991 | Yano et al. |
| 5,117,048 A | 5/1992 | Zaby et al. |
| 5,136,087 A | 8/1992 | Van Horn et al. |
| 5,286,760 A | 2/1994 | Bolton et al. |
| 5,449,818 A | 9/1995 | Biskup et al. |
| 5,763,697 A | 6/1998 | Hermann et al. |
| 5,808,157 A | 9/1998 | Langer et al. |
| 5,877,350 A | 3/1999 | Langer et al. |
| 6,043,394 A | 3/2000 | Langer et al. |
| 6,562,247 B2 | 5/2003 | Gillis et al. |
| 6,803,483 B2 | 10/2004 | Lokum et al. |
| 7,108,770 B2 | 9/2006 | Grün et al. |
| 7,118,653 B2 | 10/2006 | Brady et al. |
| 7,230,130 B2 | 6/2007 | Ströfer et al. |
| 7,253,321 B2 | 8/2007 | Hagen et al. |
| 7,521,576 B2 | 4/2009 | Schal et al. |
| 7,541,487 B2 | 6/2009 | Pohl et al. |

(Continued)

FOREIGN PATENT DOCUMENTS

| | | |
|---|---|---|
| DE | 1114820 B | 10/1961 |
| DE | 1133394 B | 7/1962 |

(Continued)

OTHER PUBLICATIONS

W. Siefken, Liebigs Ann. 562, 75-106 (1949).
G. Wegener et al. Applied Catalysis A: General 221 (2001), pp. 303 to 335.
Ullmanns Enzyklopädie der technischen Chemie [Ullmann's Encyclopedia of Industrial Chemistry], 4th ed. (1977), vol. 13, pp. 351 to 353.

(Continued)

*Primary Examiner* — Jafar F Parsa
*Assistant Examiner* — Blaine G Doletski
(74) *Attorney, Agent, or Firm* — Donald R. Palladino (57) ABSTRACT

The present invention relates to a process for producing isocyanates in process chains, each of which produce an isocyanate end product via at least one intermediate product, wherein the heat energy liberated in a first production plant in a heat-emitting operation of producing an intermediate product, an isocyanate end product or a catalyst required for a substep of the process chain (first chemical product) is at least partly utilized for generating vapour, in particular water vapour, having a pressure of 1.31 $bar_{(abs.)}$ to 1.91 $bar_{(abs.)}$ and a temperature of 107° C. to 119° C. and the thus generated vapour is employed for performing a heat-consuming operation in the preparation of another chemical product (second chemical product) in a second production plant.

15 Claims, 2 Drawing Sheets

(56) References Cited

U.S. PATENT DOCUMENTS

| | | |
|---|---|---|
| 7,547,801 B2 | 6/2009 | Pohl et al. |
| 7,615,662 B2 | 11/2009 | Pohl et al. |
| 7,649,108 B2 | 1/2010 | Schal et al. |
| 8,044,244 B2 | 10/2011 | Seidemann et al. |
| 8,097,751 B2 | 1/2012 | Koch et al. |
| 9,024,057 B2 | 5/2015 | Biskup |
| 9,067,864 B2 | 6/2015 | Sommer et al. |
| 9,150,493 B2 | 10/2015 | Lorenz et al. |
| 9,695,115 B2 | 7/2017 | Bruns et al. |
| 2006/0011463 A1 | 1/2006 | Sohn et al. |
| 2007/0265465 A1 | 11/2007 | Keggenhoff et al. |
| 2009/0240076 A1 | 9/2009 | Pohl et al. |
| 2010/0185011 A1 | 7/2010 | Carr et al. |
| 2012/0209024 A1* | 8/2012 | Bock .................. C07C 29/12 560/345 |
| 2014/0336426 A1 | 11/2014 | Benje et al. |
| 2016/0046557 A1 | 2/2016 | Guenaltay et al. |
| 2017/0066713 A1 | 3/2017 | Jaeger et al. |
| 2017/0152535 A1 | 6/2017 | Jaeger et al. |
| 2018/0334694 A1 | 11/2018 | Jäger et al. |
| 2018/0371512 A1 | 12/2018 | Jäeger et al. |

FOREIGN PATENT DOCUMENTS

| | | |
|---|---|---|
| EP | 0436443 A2 | 7/1991 |
| GB | 1452466 A | 10/1976 |

OTHER PUBLICATIONS

H. Hermann, J. Gebauer, P. Konieczny, "Industrial Nitration of Toluene to Dinitrotoluene" in ACS-Symposium, Series 623, 234-249, 1996, ed. L.F.Albright, R.V.C Carr, R.J. Schmitt.

* cited by examiner

PROCESS FOR PRODUCING ISOCYANATE AND AT LEAST ONE FURTHER CHEMICAL PRODUCT IN AN INTEGRATED PRODUCTION

CROSS-REFERENCE TO RELATED APPLICATIONS

This Application is a National Phase Application of PCT/EP2017/070675, filed Aug. 15, 2017, which claims priority to European Application No. 16184618.3, filed Aug. 17, 2016, and to European Application No. 17178902.7, filed Jun. 30, 2017, each of which is incorporated herein by reference.

FIELD

The present invention relates to a process for preparing isocyanates in process chains, in each of which isocyanate is prepared as end product via at least one intermediate, wherein the heat energy released in a first production plant in a heat-releasing operation in the preparation of an intermediate, an isocyanate end product or a catalyst required for a partial step in the process chain (first chemical product) is utilized at least partly for generation of vapor, especially of steam, at a pressure of 1.31 $bar_{(abs.)}$ to 1.91 $bar_{(abs.)}$ and a temperature of 107° C. to 119° C., and the vapor thus generated is used for the performance of a heat-consuming operation in the preparation of another chemical product (second chemical product) in a second production plant.

BACKGROUND

Industrial scale chemical processes for preparation of isocyanates and the precursors required for preparation thereof are available. The processes can be operated batchwise, semicontinuously, continuously or in a combination of one of these three variants. The processes are endothermic or exothermic and can be conducted isothermally or adiabatically. According to the isocyanate to be prepared, the process can be conducted in the gas phase or in the liquid phase, with or without solvent, or in the melt. The workup and purification of the isocyanate thus obtained can be effected by one of the standard methods in the art, for example crystallization, washing, distillation, or in a combination of these workup methods.

The quality of a process for preparing an isocyanate is firstly defined by the content of unwanted by-products in the product of the process. Secondly, the quality of a process is defined in that the whole operation of startup and production in the target state until the shutdown of the process can be executed without technical production outage and without problems that would necessitate intervention in the operation, and that there are no losses of feedstocks, intermediates or end product.

Ideally, therefore, the industrial scale plants for performance of such preparation processes are designed such that the processes run in a robust manner in the event of appropriate quality of the auxiliaries and feedstocks used and correct choice of process parameters such as pressure, temperature, ratios of amount and concentrations of the auxiliaries and feedstocks, etc. This means that, in such continuously operated large-scale plants, there will ideally be no problems such as the formation of precipitates which can settle out in plant equipment or block pipelines.

In order to further enhance economic viability, the efficiency of the energy consumption of such industrial scale plants was enhanced even at an early stage. Energy consumption can be greatly reduced by sensible heat integration between the individual plant components of a production plant. The aim is to industrially implement the sensible utilization of excess energy, for example from an adiabatic process, as far as possible.

For example, WO 2004/056 761 A1 is concerned with heat integration in a process for preparing isocyanates by reacting amines with phosgene in the presence of inert organic solvents in a reactor and subsequent workup of the reaction mixture leaving the reactor. Heat integration is implemented in such a way that the removal of solvent is effected in a two- or multistage, preferably two-stage, distillative method and the solvent is removed in a first apparatus, preferably a distillation column, at 0.1 to 15 bar, preferably 0.5 to 3 bar, and in a second apparatus or further apparatuses, preferably likewise distillation columns, at 1 to 900 mbar, preferably 50 to 500 mbar, where the heat of condensation of the solvent vapor, also referred to as vapors, from the first apparatus is used for partial or complete evaporation of solvent in the second apparatus.

In the first column, solvent vapor is removed by distillation. The liquid component obtained as bottoms discharge from this column, upstream of or within the second apparatus, is expanded to the lower pressure level of the second apparatus and is fed to the second apparatus in which the rest of the solvent is removed. The transfer of energy in the vapors from the first apparatus to the liquid phase of the second apparatus can especially be effected using a heat exchanger, for example a crossflow apparatus, in which the condensing vapors bring about the evaporation of the liquid phase from the second apparatus of the second column. It is possible here to conduct the vapors and liquid phase in co- or countercurrent. The vapors may be condensed in the shell space or in the product space of the heat exchanger. The liquid in the second column can be withdrawn from the bottom, from a tray, from a liquid collector or from the feed. There is no description of any further use of energy remaining after the internal heat integration.

EP 1 854 783 A2 is also concerned with the preparation of isocyanates. Likewise described in this application is heat integration in the recovery of solvent. In a preferred embodiment of the process, the solvent-containing stream obtained in step d) and at least partly recycled in step e) is freed of residual amounts of phosgene in a special distillation stage. More preferably, in this distillative separation of the residual amounts of phosgene, the tangible heat in the solvent stream recovered is used wholly or partly as energy source for this separation step. This can be effected, for example, in that the feed into the distillation column heats the column bottoms via a heat exchanger. Since the solvent separated by distillation is normally obtained at a temperature of >100° C., but for generation of the solution of amine in the solvent for optimal phosgenation conditions should be at <50° C., the separation of the residual amounts of phosgene can thus be combined with simultaneous cooling of the solvent. There is no description of any further use of energy remaining after the internal heat integration.

European patent application EP 2 096 102 A1 is likewise concerned with the preparation of isocyanates. What is described is an integrated process for preparing di- and polyisocyanates of the diphenylmethane series (MDI; also referred to hereinafter as a mixture of methylene diphenylene diisocyanate —(OCN)$C_6H_4$—$CH_2$—$C_6H_4$(NCO)— and polymethylene polyphenylene polyisocyanate —(OCN)$C_6H_4$—$CH_2$—[$C_6H_3$(NCO)$CH_2$—]$_x C_6H_4$(NCO), where x is a natural number ≥1), in which the salt-containing wastewater obtained in the preparation of the precursor compounds of the di- and polyamines of the diphenylmethane series (MDA; also referred to hereinafter as a mixture of methylene diphenylene diamine and polymethylene polyphenylene polyamine) is electrolyzed to chlorine, and the chlorine thus obtained is converted to phosgene which is then used in the conversion of MDA to MDI. The invention thus relates to integration by mass transfer between the production plants for MDA and MDI. The patent application does not address heat integration.

International patent application WO 2008/148608 A1 describes the entire MDI process chain proceeding from the benzene starting material, which is converted to MDI by the steps of nitration, hydrogenation, condensation with formaldehyde and acid-catalyzed rearrangement and finally phosgenation. The patent application is based on the technical object of providing a process for preparing MDI, which enables use of benzene of a lower purity than is typically used in the prior art as starting material. One proposed way of achieving this object is to use benzene of a lower purity than is typically used in the prior art as starting material. This lower purity is characterized by a content of alkyl-substituted aromatics in the benzene of 500 to 5000 ppm. Heat integration between the individual process stages of the MDI process chain is not the subject of this application.

Industrial scale production plants for chemical products are nowadays constructed in a steel skeleton designed in order to counteract the lack of space that often prevails on existing chemical sites. It is advantageous to establish various stages in a process chain (for example in the preparation of various isocyanates, the stages of nitration, hydrogenation, optional further conversion of the hydrogenation product and phosgenation) at one site in an integrated production system in order to save logistics costs. The individual production plants in such an integrated production system are typically positioned in series. Building at close quarters also entails drawbacks that have to be minimized A disadvantage is the lack of space in the construction of individual production plants in an integrated production system; there can be problems with maintenance measures (for example setting up cranes). Safety aspects such as complying with the due safety margins between production plants have to be observed. The provision of auxiliaries and feedstocks is problematic in some cases owing to cramped roads and areas between the production plants. The necessarily greater distances from central tank farms (for auxiliaries, feedstocks, products) necessitate the use of longer pipelines with larger pumps.

Energy consumption for direct or indirect process heating and cooling by vapor, by comparison with other modes of energy consumption, especially of electrical energy, is a major cost pool in the operation of industrial scale production plants, and so measures for optimizing this energy consumption offer the greatest potential for savings. Heat integration based on a pinch analysis provides a remedy here. In this way, it is possible to ascertain, for example, the optimal configuration of the feed preheating/cooling for reduction of the energy demand of columns, of waste heat vapor production and of the use of heat pumps and vapor compression, or the generation of coolant in an absorption cooler. Residual heat available in a production plant can be used at other points in the same process, or for heating of nearby administration buildings. It is also possible to use residual heat no longer suitable for vapor generation to heat buildings. Relatively low feed temperatures are sufficient for heating of buildings, and so even residual heat no longer suitable for vapor generation is utilizable. It is also conceivable to use residual heat to generate coolant in an absorption cooler.

The current prior art processes for industrial scale preparation of isocyanates and precursors thereof generally succeed in preparing the desired products with high yield and in sensibly utilizing excess energy by heat integration within individual production plants. This is frequently accomplished in such a way that excess energy from an operation within a preparation process for a chemical product is used by means of a suitable apparatus (for example a heat exchanger) for generation of vapor, especially for generation of steam, and the vapor thus obtained is used in a heat-consuming operation in the same preparation process (in this regard see also the abovementioned examples from the patent literature). However, even after maximum exploitation of this "internal" heat integration (i.e. heat integration within the production plant for a chemical product), excess "residual energy" frequently still remains. Such residual energy can generally be used to generate only vapor at a comparatively low pressure and low temperature (also colloquially called "weak vapor"). Steam of this kind is then either merely utilized for heating of administration buildings or the residual energy is lost in the form of waste heat without any sensible utilization, or even incurs additional costs, for example through requirement of air coolers for "energy destruction".

"True" heat integration with such residual energy has not been described to date in the prior art relating to preparation of isocyanates at the current state of knowledge, and has barely been described in general in the prior art:

International patent application WO 2013/083230 A1 discloses heat integration in a complex for preparation of vinyl chloride (VCM) from ethylene, hydrogen chloride and oxygen or from ethylene and chlorine via the isolated 1,2-dichloroethane (DCE) intermediate. VCM is of industrial significance as starting monomer for the preparation of polyvinyl chloride (PVC). In the process described, the heat obtained in the condensation of the top stream from a high boiler column for purification of the DCE intermediate is utilized to obtain low-pressure steam which then finds use, for example, for the operation of a stripping column for purification of the VCM or in various facilities in a downstream PVC plant. However, the individual constituents of a VCM complex or a VCM/PVC complex are not of comparable complexity to the individual production plants in an integrated isocyanate production system. The chemical processes are additionally entirely different than those in an integrated isocyanate production system. Owing to the variety of different chemical processes (examples include: chlorine production, carbon monoxide production, phosgene production, nitration including the provision of nitric acid required for the purpose, hydrogenation including the provision of the hydrogen required for the purpose, possibly condensation and rearrangement reactions, phosgenation), heat integration between individual production plants in an integrated isocyanate production system poses completely different challenges to the operators.

German patent application DE 10 2013 205 492 A1 discloses that "intrinsic vapor" at a temperature of typically 120° C. to 170° C. and an absolute pressure of typically 2 to 8 bar which is obtained in the preparation of vinyl acetate can be sent to other operations in an integrated works or can be used for heating of product pipelines or buildings. All these modes of utilization are described as disadvantageous; there is no disclosure of the kind of operations that could accept such vapor. It is an object of the application to make it possible to dispense with this mode of utilization of intrinsic vapor in favor of in-process utilization. A solution proposed is that of equipping particular columns in the process for preparation of vinyl acetate with random packings and hence enabling use of the intrinsic vapor for the energy supply of the columns thus equipped.

Further improvements in energy integration in processes for preparing isocyanates, by means of which such residual energy can be sent to a sensible use in the preparation of chemical products, would therefore be desirable. Such improvements are desirable from sustainability and environmental aspects as well.

SUMMARY

Taking account of the above, the present invention provides a process for preparing m isocyanates in m process chains, in each of which an isocyanate is prepared as end product via at least one intermediate, wherein each of the m process chains is conducted in at least 2 production plants (100 000-1, 100 000-2, . . .), namely in a first production plant (100 000-1) designed for the preparation of the at least one intermediate and in a second production plant (100 000-2) designed for the preparation of the isocyanate end product, wherein the at least 2 production plants (100 000-1, 100 000-2, . . .,) are part of an integrated production system (1 000 000), wherein a total of n chemical products selected from the group consisting of intermediates, catalysts and isocyanate end products are prepared in the integrated production system (1 000 000), where n is a natural number in the range from 2 to 40, preferably in the range from 2 to 20, more preferably in the range from 2 to 15, and where m is a natural number in the range from 1 to n, wherein, in the preparation of each of the n chemical products, at least one heat-releasing or heat-consuming operation takes place and, in the process for preparing the m isocyanates, a total of at least one heat-releasing operation and at least one heat-consuming operation take place, wherein
(i) the heat energy released in a heat-releasing operation in the preparation of one of the chemical products in a first production plant (100 000-1) is utilized at least partly for generation of vapor, especially of steam, at a pressure of 1.31 bar$_{(abs.)}$ to 1.91 bar$_{(abs.)}$ and a temperature of 107° C. to 119° C.;
(ii) the vapor generated in (i) is used for the performance of a heat-consuming operation in the preparation of a chemical product different than the chemical product prepared in step (i), where the preparation of this chemical product different than the chemical product prepared in step (i) takes place in a second production plant (100 000-2), wherein the vapor generated in (i) is guided from the vapor-releasing point in step (i) via a pipeline to the position of the vapor-consuming operation in step (ii).

DETAILED DESCRIPTION

An integrated production system (1 000 000) in the context of the present invention refers to an integrated system consisting of at least 2 production plants (100 000-1, 100 000-2, . . .), each production plant (100 000-1, 100 000-2, . . .) having been designed for the preparation of at least one chemical product. In an integrated production system (1 000 000) of the invention, at least 2 chemical products are prepared, namely the isocyanate end product and at least one intermediate. In this simplest conceivable configuration of the invention, m=1 (preparation of exactly 1 isocyanate in exactly one process chain), and n=2 (preparation of two chemical products, namely one intermediate and the isocyanate end product). One example of such a configuration of the invention is an integrated production system (1 000 000) composed of a first production plant (100 000-1) in which dinitrotoluene is hydrogenated to tolylenediamine, and a second production plant (100 000-2) in which tolylenediamine is phosgenated to give tolylene diisocyanate. The number n denotes the number of chemical products prepared overall in the integrated production system (1 000 000). The number of chemical products actually processed in the integrated production system (1 000 000) is greater, namely at least by the number of starting materials prepared outside the integrated production system (for example bought in). It is also possible to provide particular auxiliary reagents from outside, such that they do not count as chemical products in the context of the invention.

A production plant (100 000) consists of the facilities required for the preparation and, if necessary, purification of the chemical product prepared therein. It is a feature of an integrated production system (1 000 000) in the context of the invention that every production plant (100 000) that forms part of it is coupled for energy purposes to at least one other production plant (100 000). The number of production plants (100 000) may be less than the number n of chemical products, but is not greater (i.e. is not more than n).

Chemical products in the context of the invention are not only the m isocyanate end products but all intermediates from the m process chains that are prepared in the integrated production system (1 000 000) and any catalysts required for the individual chemical conversions if they are prepared in the integrated production system (1 000 000) (e.g. hydrochloric acid as the rearrangement catalyst in the preparation of methylene diphenylene diisocyanate, polymethylene polyphenylene polyisocyanate and/or mixtures of the two if hydrochloric acid is not bought in completely but at least partly prepared on site).

The process of the invention comprises m process chains. Such a process chain in the context of the invention means the sequence of chemical conversions required for preparation of the desired isocyanate end product proceeding from a starting material provided via at least one intermediate. Heat integration can take place here between these process chains or within one process chain, but in that case between different partial steps in this process chain (and not within one and the same partial step). Examples of such process chains in the context of the invention are (in schematic and simplified form):

(α) A) toluene→dinitrotoluene;
B) dinitrotoluene→tolylenediamine;
C) tolylenediamine→tolylene diisocyanate; —first process chain comprising partial steps A) to C) and tolylene diisocyanate, the isocyanate end product;
(β) A) benzene→nitrobenzene;
B) nitrobenzene→aniline;

C) aniline→mixture of methylene diphenylene diamine and polymethylene polyphenylene polyamine (MDA);
D) MDA→mixture of methylene diphenylene diisocyanate and polymethylene polyphenylene polyisocyanate (MDI); —second process chain comprising partial steps A) to D) and MDI, the isocyanate end product.

Heat integration according to the invention can then take place between process chain (1) and process chain (2) or between different partial steps A) to C) or A) to D) within one of the process chains (α) and (β).

According to the invention, at least at one point in the process or at one point in the integrated production system, vapor at a pressure of 1.31 $bar_{(abs.)}$ to 1.91 $bar_{(abs.)}$ and a temperature of 107° C. to 119° C. (referred to in industrial jargon as "weak vapor") is produced. Suitable pressure measuring instruments for determination of the pressure are known to those skilled in the art. Particular mention should be made here of membrane pressure transmitters, which feature high accuracy. Instruments of this kind are supplied, for example, by Wika, by Endress+Hauser or by Emerson. It has been found that, in cases where sensible use of vapor in the abovementioned temperature and pressure range is not completely possible, if at all, in that preparation process for a chemical product in which the vapor is obtained, it can nevertheless sensibly be used in the production process for another chemical product. The inventive procedure of using the vapor generated in (i) for the performance of a heat-consuming operation in the preparation of a chemical product other than the chemical product prepared in step (i) also encompasses the case that just a portion of the vapor generated is used for the performance of a heat-consuming operation in the preparation of a chemical product other than the chemical product prepared in step (i) and the rest is sent to another use. It is preferable in accordance with the invention to use at least 30.0%, more preferably at least 50.0%, even more preferably at least 70.0%, very exceptionally preferably at least 90.0%, of the vapor generated in step (i) for performance of the heat-consuming operation in step (ii). It is most exceptionally preferred to use the vapor generated in step (i) completely for performance of the heat-consuming operation in step (ii).

The pipeline from step (ii) of the process of the invention, in all embodiments of the invention, is preferably manufactured from steel, for example black steel or stainless steel. Particular preference is given to black steel.

A heat-releasing operation in the context of the present invention may be either an exothermic chemical reaction or a physical operation, for example the liquefaction of a gaseous product with release of heat of condensation. Accordingly, a heat-consuming operation in the context of the present invention may be either an endothermic chemical reaction or a physical operation, for example the evaporation of a liquid starting material or intermediate with supply of heat. The vapor can be rendered utilizable in step (ii) of the process of the invention for performance of the heat-consuming operation by indirect heating (i.e. without direct contact of the vapor with the chemical compounds—starting materials, intermediates, end product, auxiliary reagents and the like—in the heat-consuming operation, for example by heating by means of a heat exchanger) or by direct input of vapor (i.e. by mixing the vapor with the chemical compounds—starting materials, intermediates, end product, auxiliary reagents and the like—in the heat-consuming operation, for example by supplying stripping vapor to a column).

Suitable vapor in the context of the present invention is any liquid that can be evaporated with the residual energy available to give vapor at a pressure and a temperature within the range of the invention, and the vapor of which is sufficiently inert toward the materials used in apparatuses and pipelines. If the vapor is rendered utilizable for performance of the heat-consuming operation by direct input of vapor, it should also be ensured that there are no unwanted reactions with the chemical compounds in the heat-consuming operation, which can limit the choice of suitable vapor sources. Particular preference is given in accordance with the invention to steam. In all embodiments of the invention, therefore, in the at least one heat-releasing operation, preference is given to producing steam which is used for performance of the at least one heat-consuming operation, either by means of indirect heating or by means of direct input of vapor. The water required for the purpose may come from various sources. Especially suitable is fresh water from the existing water grid, drinking water, demineralized water and steam condensate, preference being given to water qualities with a negligible salt content such as demineralized water and steam condensate, since it is possible through the use thereof to avoid lime deposits on apparatuses and pipelines.

There follows firstly a brief summary of various possible embodiments of the invention:

In a first embodiment of the invention, which can be combined with all other embodiments, the isocyanate end product is selected from the group consisting of methylene diphenylene diisocyanate, polymethylene polyphenylene polyisocyanate, mixtures of methylene diphenylene diisocyanate and polymethylene polyphenylene polyisocyanate, tolylene diisocyanate, xylylene diisocyanate, pentane 1,5-diisocyanate, hexamethylene diisocyanate, isophorone diisocyanate and naphthyl diisocyanate.

In a second embodiment of the invention, which can be combined with all embodiments which include the formation of an aromatic isocyanate,
in a first process chain (α)
A) in a first process stage an aromatic hydrocarbon, especially toluene, is nitrated to give an aromatic nitro compound, especially dinitrotoluene;
B) the aromatic nitro compound, especially dinitrotoluene, is hydrogenated in a second process stage by hydrogenation to give an aromatic amine, especially tolylenediamine;
C) the aromatic amine, especially tolylenediamine, is converted in a third process stage by phosgenation to give the aromatic isocyanate end product, especially tolylene diisocyanate;
and/or
in a second process chain (β)
A) in a first process stage an aromatic hydrocarbon, especially benzene, is nitrated to give an aromatic nitro compound, especially nitrobenzene;
B) the aromatic nitro compound, especially nitrobenzene, is hydrogenated in a second process stage by hydrogenation to give an aromatic amine, especially aniline;
C) the aromatic amine, especially aniline, is converted in a third process stage to another aromatic amine, especially methylene diphenylene diamine, polymethylene polyphenylene polyamine and/or mixtures of methylene diphenylene diamine and polymethylene polyphenylene polyamine;
D) the aromatic amine, especially methylene diphenylene diamine, polymethylene polyphenylene polyamine and/or mixtures of methylene diphenylene diamine and polymethylene polyphenylene polyamine, is converted in a fourth process stage by phosgenation to give the aromatic isocyanate end product, especially methylene diphenylene diisocyanate, polymethylene polyphenylene polyisocyanate and/or mixtures of methylene diphenyl diisocyanate and polymethylene polyphenylene polyisocyanate.

In a third embodiment of the invention, which is a particular configuration of the second embodiment, the phosgenation in process stage (α) C) and/or in process stage (β) D) comprises the following:
I) reacting the amine (2) to be phosgenated with phosgene (3) in the liquid phase and separating the process product obtained into a liquid stream (60) comprising the crude isocyanate and solvent, and a gaseous stream (70) comprising phosgene and hydrogen chloride;
II) separating the liquid stream (60) from step I) into a liquid stream (80) comprising solvent and crude isocyanate, and a gaseous stream (90) comprising phosgene and hydrogen chloride in a distillation apparatus (2100);
III) separating the liquid stream (80) into a gaseous stream (110) comprising solvent and a liquid stream (100) comprising crude isocyanate in a distillation apparatus (2200);
IV) separating the gaseous stream (110), after it has been at least partly liquefied in a condenser (2310), into a liquid stream (120) comprising solvent and a gaseous stream (130) comprising phosgene in a distillation apparatus (2300);
V) obtaining a liquid isocyanate stream (140) from the liquid stream (100), resulting in a gaseous stream (150) comprising secondary components and optionally solvent, in a distillation apparatus (2400), optionally comprising a step V.1) the removal of polymeric isocyanate fractions in an upstream unit for polymer removal (2410) as stream (141).

In a fourth embodiment of the invention, which is a particular configuration of the third embodiment, the process comprises process chain (β), wherein the amine to be phosgenated in process stage (β) D) is a mixture of methylene diphenylene diamine and polymethylene polyphenylene polyamine, wherein step V.1) is also conducted and hence the isocyanate end product is obtained in the two streams 140 and 141, wherein stream 140 comprises methylene diphenylene diisocyanate and stream 141 a mixture of methylene diphenylene diisocyanate and polymethylene polyphenylene polyisocyanate.

In a fifth embodiment of the invention, which is a particular configuration of the fourth embodiment, the heat-releasing operation from step (i) is the at least partial liquefaction of the gaseous stream (110) in the condenser (2310), and the vapor generated by the release of heat is guided into process stage (β) C).

In a sixth embodiment of the invention, which is a particular configuration of the fifth embodiment, process stage (β) C) comprises the following steps:
IA) reacting aniline and formaldehyde in a reactor (3000) in the absence of an acidic catalyst to form an animal, followed by separating the reaction mixture obtained into an aqueous phase and an organic phase comprising the animal in a phase separation unit integrated into the reactor or in a separate phase separation apparatus (4000);
IIA) reacting at least a portion of the organic phase comprising the animal which is obtained in step IA) in a reactor (5000) with acid, with reaction of the animal to give a mixture of methylene diphenylene diamine and polymethylene polyphenylene polyamine;
or
IB) reacting aniline and acid in a reactor;
IIB) reacting at least a portion of the reaction mixture obtained in step IB) in a reactor with formaldehyde to give a mixture of methylene diphenylene diamine and polymethylene polyphenylene polyamine;
III) neutralizing the reaction mixture obtained in step IIA) or IIB) in a reactor (6000);
IV) separating the neutralized reaction mixture obtained in step III) into an organic phase comprising a mixture of methylene diphenylene diamine and polymethylene polyphenylene polyamine and into an aqueous phase in a separation vessel (7000);
V) washing the organic phase with washing liquid in a wash vessel (8000);
VI) separating the mixture obtained in step V) into an organic phase comprising a mixture of methylene diphenylene diamine and polymethylene polyphenylene polyamine and into an aqueous phase in a separation vessel (7000);
VII) distilling the organic phase from step VI) in a distillation apparatus (10000) comprising a first distillation stage (10000-1) for removal of a water- and aniline-containing stream and a second distillation stage (10000-2) for further purification of the process product remaining in the first stage after removal of the water- and aniline-containing stream to obtain a mixture of methylene diphenylene diamine and polymethylene polyphenylene polyamine, with optional use of stripping vapor in the second stage (10000-2) for direct transfer of heat;
VIII) optionally separating methylene diphenylene diamine from the mixture of methylene diphenylene diamine and polymethylene polyphenylene polyamine obtained in step VII).

In a seventh embodiment of the invention, which is a particular configuration of the sixth embodiment, process stage (β) C) additionally comprises the following:
IX) workup
of the aqueous phase from step IA) or
of the aqueous phase from step IV) or
of the aqueous phase from step VI) or
of the water- and aniline-containing stream from step VII) or
of a mixture of two or more of the aforementioned aqueous process products
in a wastewater workup unit (11000) comprising a wastewater collection vessel (11000-1), optionally a wastewater heater (11000-2), a separation vessel (11000-3), optionally an extraction vessel (11000-4) and a wastewater distillation column (11000-5);
wherein the heat-consuming operation from step (ii) is selected from the group consisting of:
the separation of the water- and aniline-containing stream from the organic phase from step VI) in the distillation stage (10000-1),
the further purification of the process product remaining in the first distillation stage (10000-1) after removal of the water- and aniline-containing stream in the distillation stage (10000-2), where, in the case of use of stripping vapor for direct heat transfer in (10000-2), this stripping vapor comprises the vapor generated in step (i) and preferably consists solely of the vapor generated in step (i),
if the wastewater heater (11000-2) is present, the heating of this wastewater heater (11000-2), and
combinations of two or more of the aforementioned operations.

In an eighth embodiment of the invention, which is a particular configuration of the sixth and seventh embodiments, the process additionally comprises the process stage of preparing hydrochloric acid as a further chemical product, wherein the hydrochloric acid is prepared by absorption of hydrogen chloride in water or 0.1% to 20% hydrochloric acid in an absorption column, wherein the hydrochloric acid thus prepared is used as acid in step (β) C) IIA) or (β) C) IB), wherein the heat-consuming operation is the direct or indirect heating of the bottom of the absorption column from the process stage for preparation of hydrochloric acid.

In a ninth embodiment of the invention, which is a particular configuration of the second embodiment, the phosgenation in process stage (α) C) and/or in process stage (β) D) comprises the following:

0) providing gaseous phosgene (3) by evaporating liquid phosgene;
I) evaporating the amine (2) to be phosgenated, reacting the evaporated amine with gaseous phosgene (3) from step 0) in the gas phase, stopping the reaction by contacting with a solvent-containing stream at a temperature below the boiling point of the amine and separating the process product obtained into a liquid stream (60) comprising the crude isocyanate and solvent and a gaseous stream (70) comprising phosgene and hydrogen chloride;
II) separating the liquid stream (60) from step I) into a liquid stream (80) comprising solvent and crude isocyanate, and a gaseous stream (90) comprising phosgene and hydrogen chloride in a distillation apparatus (2100);
III) separating the liquid stream (80) into a gaseous stream (110) comprising solvent and a liquid stream (100) comprising crude isocyanate in a distillation apparatus (2200);
IV) separating the gaseous stream (110), after it has been at least partly liquefied in a condenser (2310), into a liquid stream (120) comprising solvent and a gaseous stream (130) comprising phosgene in a distillation apparatus (2300);
V) obtaining a liquid isocyanate stream (140) from the liquid stream (100), giving a gaseous stream (150) comprising secondary components with or without solvents and a mixture of polymeric components and monomeric isocyanate as stream (143), in a distillation apparatus (2400) preferably designed as a dividing wall column.

In a tenth embodiment of the invention, which is a particular configuration of the ninth embodiment, the process comprises process chain (α), wherein the heat-consuming operation from step (ii) is at least one partial step of the evaporation of liquid phosgene in step 0) and wherein the heat-releasing operation from step (i) originates from process stage (α) B).

In an eleventh embodiment of the invention, which is a particular configuration of the second embodiment, the process comprises process chain (α) and process stage (β), wherein
the at least one heat-releasing operation from step (i) is part of process chain (α) and the at least one heat-consuming operation from step (ii) is part of process chain (β)
or in which
the at least one heat-releasing operation from step (i) is part of process chain (β) and the at least one heat-consuming operation from step (ii) is part of process chain (α).

In a twelfth embodiment of the invention, which may be combined with all other embodiments,
in step (i) the vapor is generated by means of an apparatus for indirect heat transfer which is preferably selected from the group consisting of natural circulation boilers, forced circulation boilers, forced passage boilers, shell and tube heat exchangers, U-tube heat exchangers, double tube coil heat exchangers, plate heat exchangers, tube heat exchangers, spiral heat exchangers and inserted condensers or in step (ii) the amount of heat required for the performance of the heat-consuming operation is provided by means of an apparatus for indirect heat transfer which is preferably selected from the group consisting of natural circulation evaporators, forced circulation evaporators, inserted evaporators, self-circulation evaporators, rising-film evaporators, falling-film evaporators, plate evaporators, helical tube evaporators, thin-film evaporators, short-path evaporators, shell and tube heat exchangers and spiral heat exchangers or in step (i) the vapor is generated by means of an apparatus for indirect heat transfer which is preferably selected from the group consisting of natural circulation boilers, forced circulation boilers, forced passage boilers, shell and tube heat exchangers, U-tube heat exchangers, double tube coil heat exchangers, plate heat exchangers, tube heat exchangers, spiral heat exchangers and inserted condensers, and in step (ii) the amount of heat required for the performance of the heat-consuming operation is provided by means of an apparatus for indirect heat transfer which is preferably selected from the group consisting of natural circulation evaporators, forced circulation evaporators, inserted evaporators, self-circulation evaporators, rising-film evaporators, falling-film evaporators, plate evaporators, helical tube evaporators, thin-film evaporators, short-path evaporators, shell and tube heat exchangers and spiral heat exchangers.

In a thirteenth embodiment of the invention, which may be combined with all other embodiments, by adjusting
the size of the vapor stream guided from the vapor-releasing point in step (i) to the position of the heat-consuming operation in step (ii) or
the nominal width of the pipeline used in step (ii) or
the size of the vapor stream guided from the vapor-releasing point in step (i) to the position of the heat-consuming operation in step (ii) and the nominal width of the pipeline from step (iii),
a velocity of the vapor stream in the pipeline, calculated from the quotient of the volume flow rate of the vapor and the cross section of the pipeline, in the range from 10.0 m/s to 40.0 m/s is brought about.

In a fourteenth embodiment of the invention, which may be combined with all other embodiments, the pipeline has a length of not more than 400 m and an internal diameter $d_i$ in the range from 300.0 mm to 1000 nm.

The embodiments briefly outlined above and further possible configurations of the invention are elucidated in detail hereinafter. Various embodiments may be combined with one another as desired, unless the opposite is apparent to the person skilled in the art from the context.

Examples of di- and polyisocyanates that should be mentioned here as isocyanates preparable by the process of the invention include aromatic di- and polyisocyanates, for example methylene diphenylene diisocyanate (mMDI) as specific isomers or as isomer mixture, polymethylene polyphenylene polyisocyanate (pMDI), mixtures of methylene diphenylene diisocyanate and polymethylene polyphenylene polyisocyanate (MDI), tolylene diisocyanate (TDI) as pure isomers or isomer mixture, isomers of xylylene diisocyanate (XDI), isomers of diisocyanatobenzene, xylene 2,6-isocyanate, naphthylene 1,5-diisocyanate (1,5-NDI), diisocyanates based on aliphatic or cycloaliphatic hydrocarbons having 2 to 18 carbon atoms, for example butane 1,4-diisocyanate, pentane 1,5-diisocyanate (PDI), hexane 1,6-diisocyanate (HDI), octane 1,8-diisocyanate, nonane 1,9-diisocyanate, decane 1,10-diisocyanate, 2,2-dimethylpentane 1,5-diisocyanate, 2-methylpentane 1,5-diisocyanate (MPDI), 2,4,4(or 2,2,4)-trimethylhexane 1,6-diisocyanate (TMDI), cyclohexane 1,3- and 1,4-diisocyanate, 1-isocyanato-3,3,5-trimethyl-5-isocyanatomethylcyclohexane (IPDI), 2,4- or 2,6-diisocyanato-1-methylcyclohexane (H6-TDI), 1-isocyanato-1-methyl-4(3)-isocyanatomethylcyclohexane (AMCI), 1,3 (and/or 1,4)-bis(isocyanatomethyl)cyclohexane, bis(isocyanatomethyl)norbornane (NBDI), 4,4'(and/or 2,4')-diisocyanatodicyclohexylmethane, and (cyclo)aliphatic triisocyanates having up to 22 carbon atoms, for example triisocyanatocyclohexane, tris(isocyanatomethyl)cyclohexane, triisocyanatomethylcyclohexane, 1,8-diisocyanato-4-(isocyanatomethyl)octane, undecane 1,6,11-triisocyanate, 1,7-diisocyanato-4-(3-isocyanatopropyl)heptane, 1,6-diisocyanato-3-(isocyanatomethyl)hexane or 1,3,5-tris(isocyanatomethyl)cyclohexane.

The amines corresponding to the above polyisocyanates are aromatic di- and polyamines, for example methylene diphenylene diamine (mMDA) as isomers or as isomer mixture, polymethylene polyphenylene polyamine (pMDA), mixtures of methylene diphenylene diamine and polymethylene polyphenylene polyamine (MDA), tolylenediamine (TDA) as pure isomers or isomer mixture, isomers of xylylenediamine (XDA), isomers of diaminobenzene, 2,6-xylidine, naphthylene-1,5-diamine (1,5-NDA), diamines based on aliphatic or cycloaliphatic hydrocarbons having 2 to 18 carbon atoms, for example 1,4-diaminobutane, 1,5-diaminopentane (PDA), 1,6-diaminohexane (HDA), 1,8-diaminooctane, 1,9-diaminononane, 1,10-diaminodecane, 2,2-dimethyl-1,5-diaminopentane, 2-methyl-1,5-pentanediamine (MPDA), 2,4,4(or 2,2,4)-trimethyl-1,6-diaminohexane (TMDA), 1,3- and 1,4-diaminocyclohexane, 1-amino-3,3,5-trimethyl-5-aminomethylcyclohexane (IPDA), 2,4- or 2,6-diamino-1-methylcyclohexane (H6-TDA), 1-amino-1-methyl-4(3)-aminomethylcyclohexane (AMCA), 1,3(and/or 1,4)-bis(aminomethyl)cyclohexane, bis(aminomethyl)norbornane (NBDA), 4,4'(and/or 2,4')-diaminodicyclohexylmethane, (cyclo)aliphatic triamines having up to 22 carbon atoms, for example triaminocyclohexane, tris(aminomethyl)cyclohexane, triaminomethylcyclohexane, 1,8-diamino-4-(aminomethyl)octane, undecane-1,6,11-triamine, 1,7-diamino-4-(3-aminopropyl)heptane, 1,6-diamino-3-(aminomethyl)hexane or 1,3,5-tris(aminomethyl)cyclohexane.

The industrial scale preparation of the isocyanates listed above by reacting the corresponding amines with phosgene has fundamentally long been known from the prior art, the reaction being conducted in the gas or liquid phase and batchwise or continuously (W. Siefken, Liebigs Ann. 562, 75-106 (1949)). Processes for preparing organic isocyanates from primary amines and phosgene have already been described many times before; see, for example, G. Wegener et al. Applied Catalysis A: General 221 (2001), pages 303 to 335, Elsevier Science B. V. and Ullmanns Enzyklopädie der technischen Chemie [Ullmann's Encyclopedia of Industrial Chemistry], 4th ed. (1977), volume 13, pages 351 to 353.

In terms of production volumes, MDI and TDI are the most important isocyanate products worldwide.

Modern industrial scale preparation of MDI is continuous, and the reaction is preferably conducted as an adiabatic phosgenation as described in EP 1 616 857 B2 and EP 1 873 142 B1. The workup of the crude MDI is described by way of example in U.S. Pat. No. 5,136,087 (B), EP 1 854 783 A2, EP 1 475 367 B1 or else in EP 1 686 112 A1. MDI is initially obtained in the form of a mixture of methylene diphenylene diisocyanate and polymethylene polyphenylene polyisocyanate. Irrespective of whether pure monomer components (mMDI) are separated from this mixture or not, MDI is considered to be one (1) chemical product in the context of this invention.

The continuous production of TDI in industry is effected in the gas phase, as described, for example, in EP-A-2 196 455, EP-A-0 289 840, EP-A-0 570 799, EP-B-1 935 875 and EP-B-1 935 876, or in the liquid phase, as described, for example, in EP 0 322 647 B1, WO 2013/139703 A1, EP 314 985 B1, EP 1 371 636 B1, EP 1 371 635 B1 and EP 1 413 571 B1.

The precursor of MDI is MDA. MDA in turn is prepared by condensation of aniline and formaldehyde. Aniline is obtained by hydrogenation of nitrobenzene. Nitrobenzene in turn arises through nitration of benzene with nitric acid, with benzene constituting the petrochemical basis for preparation of MDI via the individual intermediates. Alternatively, aniline can also be obtained by biochemical processes as described in WO 2015/124686 A1 and WO 2015/124687 A1 and as yet unpublished patent applications EP 15195527.5 and EP 16157777.0.

The continuous or batchwise preparation of MDA is disclosed, for example, in EP 1 616 890 A1, U.S. Pat. No. 5,286,760, EP-A-451442 and WO-A-99/40059.

The continuous preparation of aniline in isothermal or adiabatic mode is effected on the industrial scale generally by catalytic hydrogenation of nitrobenzene, as described, for example, in GB 1 452 466 A1, EP 0 011 090 A1 or EP 0 944 578 A2 (isothermal mode) and in EP 0 696 574 B1, EP 0 696 573 B1, EP 1 882 681 A1 (adiabatic mode). As well as the processes mentioned with stationary catalyst beds, those having fluidized catalyst beds have also been described, for example in DE 1114820 B, DE 1133394 B or WO 2008/034770 A1.

The processes for industrial scale preparation of nitrobenzene that are standard nowadays correspond essentially to the concept of adiabatic nitration of benzene by a mixture of sulfuric acid and nitric acid, which is generally referred to as mixed acid. Such a process was claimed for the first time in U.S. Pat. No. 2,256,999 and is described in current embodiments, for example, in EP 0 436 443 B1, EP 0 771 783 B1 and U.S. Pat. No. 6,562,247 B2. Isothermal processes for nitration of benzene with mixed acid are also known, as described, for example, in EP 0 156 199 B1.

The precursor of TDI is TDA. TDA in turn is obtained by hydrogenation of dinitrotoluene (DNT). DNT in turn arises through nitration of toluene, which constitutes the petrochemical basis for preparation of TDI via the individual intermediates.

The modern continuous preparation of TDA in isothermal and/or adiabatic mode is effected on the industrial scale generally by catalytic hydrogenation of DNT, as described, for example, in detail in WO 2011/086050 A1 and references cited therein.

The preparation of dinitrotoluene by nitration of toluene with nitrating acid (mixture of nitric acid and sulfuric acid) has already been the subject of numerous publications and patent applications (Ullmanns Enzyklopedie der technischen Chemie, 4th edition, volume 17, page 391 ff, 1979, Verlag Chemie Weinheim/New York). The industrial scale preparation is effected by predominantly isothermal means with nitric acid in the presence of sulfuric acid as catalyst in continuous mode, as described, for example, in H. Hermann, J. Gebauer, P. Konieczny, "Industrial Nitration of Toluene to Dinitrotoluene" in ACS-Symposium, Series 623, 234-249, 1996, ed. L. F. Albright, R. V. O Carr, R. J. Schmitt.

The preparation of nitric acid is described in numerous publications and patent applications. The dimensions of the plant are typically such that various process chains, for example a TDI process chain and an MDI process chain, can be supplied from one nitric acid plant.

More preferably in accordance with the invention, the isocyanate is selected from the group consisting of methylene diphenylene diisocyanate, polymethylene polyphenylene polyisocyanate, mixtures of methylene diphenylene diisocyanate and polymethylene polyphenylene polyisocyanate, tolylene diisocyanate, xylylene diisocyanate, pentane 1,5-diisocyanate, hexamethylene diisocyanate, isophorone diisocyanate and naphthyl diisocyanate.

For aromatic isocyanates, it is preferably the case that in a first process chain (α)
A) in a first process stage an aromatic hydrocarbon, especially toluene, is nitrated to give an aromatic nitro compound, especially dinitrotoluene;
B) the aromatic nitro compound, especially dinitrotoluene, is hydrogenated in a second process stage by hydrogenation to give an aromatic amine, especially tolylenediamine;
C) the aromatic amine, especially tolylenediamine, is converted in a third process stage by phosgenation to give the aromatic isocyanate product, especially tolylene diisocyanate;
and/or
in a second process chain (β)
A) in a first process stage an aromatic hydrocarbon, especially benzene, is nitrated to give an aromatic nitro compound, especially nitrobenzene;
B) the aromatic nitro compound, especially nitrobenzene, is hydrogenated in a second process stage by hydrogenation to give an aromatic amine, especially aniline;
C) the aromatic amine, especially aniline, is converted in a third process stage to another aromatic amine, especially methylene diphenylene diamine, polymethylene polyphenylene polyamine and/or mixtures of methylene diphenylene diamine and polymethylene polyphenylene polyamine;
D) the aromatic amine, especially methylene diphenylene diamine, polymethylene polyphenylene polyamine and/or mixtures of methylene diphenylene diamine and polymethylene polyphenylene polyamine, is converted in a fourth process stage by phosgenation to give the aromatic isocyanate end product, especially methylene diphenylene diisocyanate, polymethylene polyphenylene polyisocyanate and/or mixtures of methylene diphenylene diisocyanate and polymethylene polyphenylene polyisocyanate.

Figure 1:
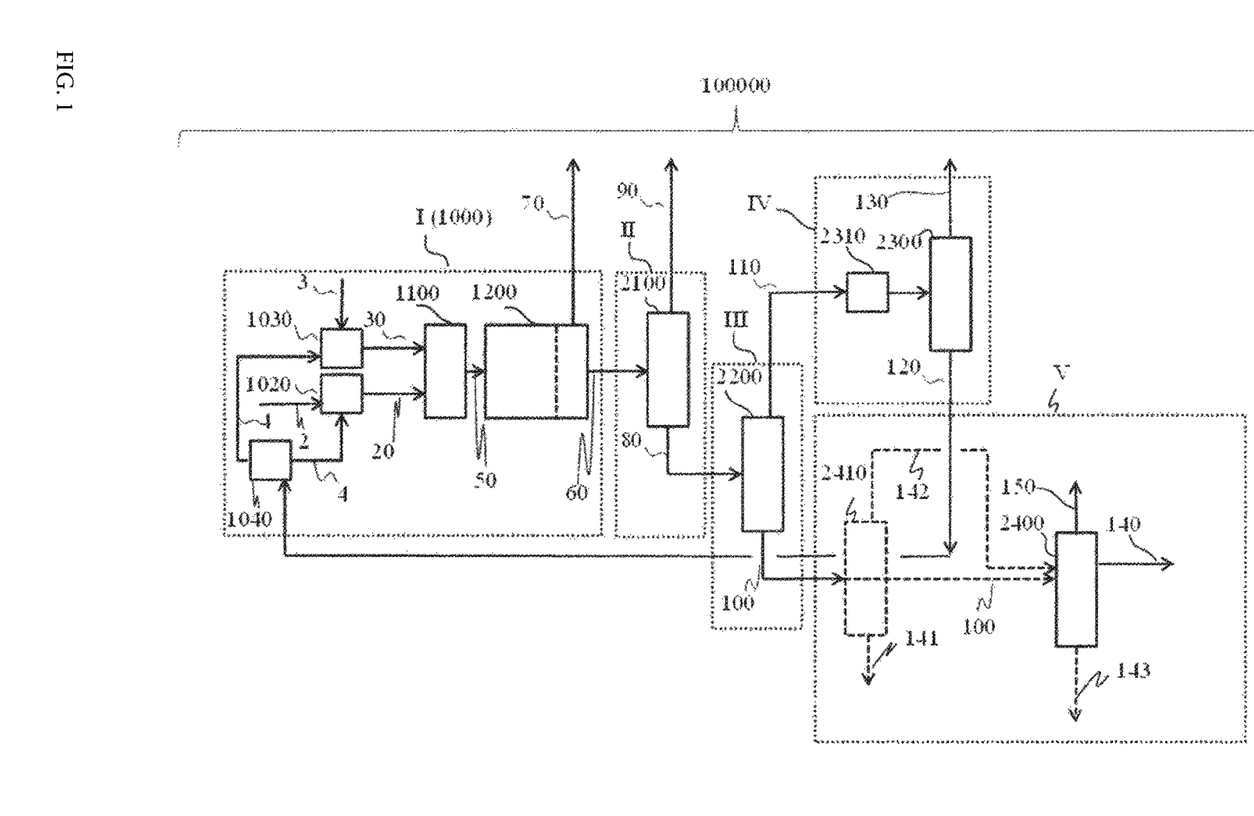
FIG. 1 illustrates an exemplary apparatus configuration of the process stage of phosgenation in which the phosgenation takes place in the liquid phase.

In a preferred configuration of the invention relating to the production of aromatic isocyanates, the phosgenation takes place in the liquid phase (in this regard see also FIG. 1). More particularly, this embodiment relates to a process in which the phosgenation in process stage (α) C) and/or in process stage (β) D) comprises the following:
I) reacting the amine (2) to be phosgenated with phosgene (3) in the liquid phase and separating the process product obtained into a liquid stream (60) comprising the crude isocyanate and solvent, and a gaseous stream (70) comprising phosgene and hydrogen chloride;
II) separating the liquid stream (60) from step I) into a liquid stream (80) comprising solvent and crude isocyanate, and a gaseous stream (90) comprising phosgene and hydrogen chloride in a distillation apparatus (2100);
III) separating the liquid stream (80) into a gaseous stream (110) comprising solvent and a liquid stream (100) comprising crude isocyanate in a distillation apparatus (2200);
IV) separating the gaseous stream (110), after it has been at least partly liquefied in a condenser (2310), into a liquid stream (120) comprising solvent and a gaseous stream (130) comprising phosgene in a distillation apparatus (2300);
V) obtaining a liquid isocyanate stream (140) from the liquid stream (100), resulting in a gaseous stream (150) comprising secondary components and optionally solvent, in a distillation apparatus (2400), optionally comprising a step V.1) the removal of polymeric isocyanate fractions in an upstream unit for polymer removal (2410) as stream (141).

A preferred apparatus configuration of the process stage of phosgenation in this embodiment is shown by FIG. 1. Apparatuses for workup of the gaseous streams (70, 90, 130, 150) are not shown for the sake of simplicity because they are of no significance for understanding of the process of the invention. Single-digit to three-digit reference numerals denote streams of matter having the meaning given above. All apparatuses have been given four-digit reference numerals. The reference numerals mean:
1000: reaction zone;
1020: unit for providing an amine (2) in the form of an amine solution (20) in a solvent (4);
1030: unit for providing phosgene (3) in the form of a phosgene solution (30) in a solvent (4);
1040: unit for providing a solvent (4);
1100: mixing unit for mixing amine solution (20) with phosgene solution (20) and optionally further solvent (4);
1200: reaction space for conducting the phosgenation, with an optional downstream separator unit (1210), where the reaction space or the separation apparatus have been provided with outlet conduits for the liquid stream (60) and the gaseous stream (70);
2100: distillation apparatus ("dephosgenation column") for separation of the liquid stream (60) into a liquid stream (80) and a gaseous stream (90);
2200: distillation apparatus ("solvent column") for separation of the liquid stream (80) into a gaseous stream (110) and a liquid stream (100);
2300: distillation apparatus ("solvent stripper") for separation of the gaseous stream (110), after it has been liquefied in a condenser (2310), into a liquid stream (120) and a gaseous stream (130);
2400: distillation apparatus (2400) for obtaining a liquid isocyanate stream (140) from the liquid stream (100) to obtain a gaseous stream (150) comprising secondary components, with or without solvent,
optionally comprising
2410: an upstream unit for polymer removal ("polymer removal", PMA) for removal of polymeric isocyanate fractions (141).

This embodiment of the process of the invention is especially suitable for the preparation of methylene diphenylene diisocyanate and a mixture of methylene diphenylene diisocyanate and polymethylene polyphenylene polyisocyanate in process chain (β). In this configuration of the process, the amine envisaged for phosgenation is then a mixture of methylene diphenylene diamine and polymethylene polyphenylene polyamine, wherein step V.1) ("polymer removal") is conducted and hence the isocyanate end product is obtained in the two streams 140 and 141, wherein stream 140 is methylene diphenylene diisocyanate and stream 141 a mixture of methylene diphenylene diisocyanate and polymethylene polyphenylene polyisocyanate.

In this embodiment of the process of the invention, the heat-releasing operation from step (i) is preferably the at least partial liquefaction of the gaseous stream (110) in the condenser (2310), wherein the vapor generated by the release of heat is guided into the process stage for preparation of the amine to be phosgenated, i.e. the MDA preparation (process stage (β) C)).

Figure 2:
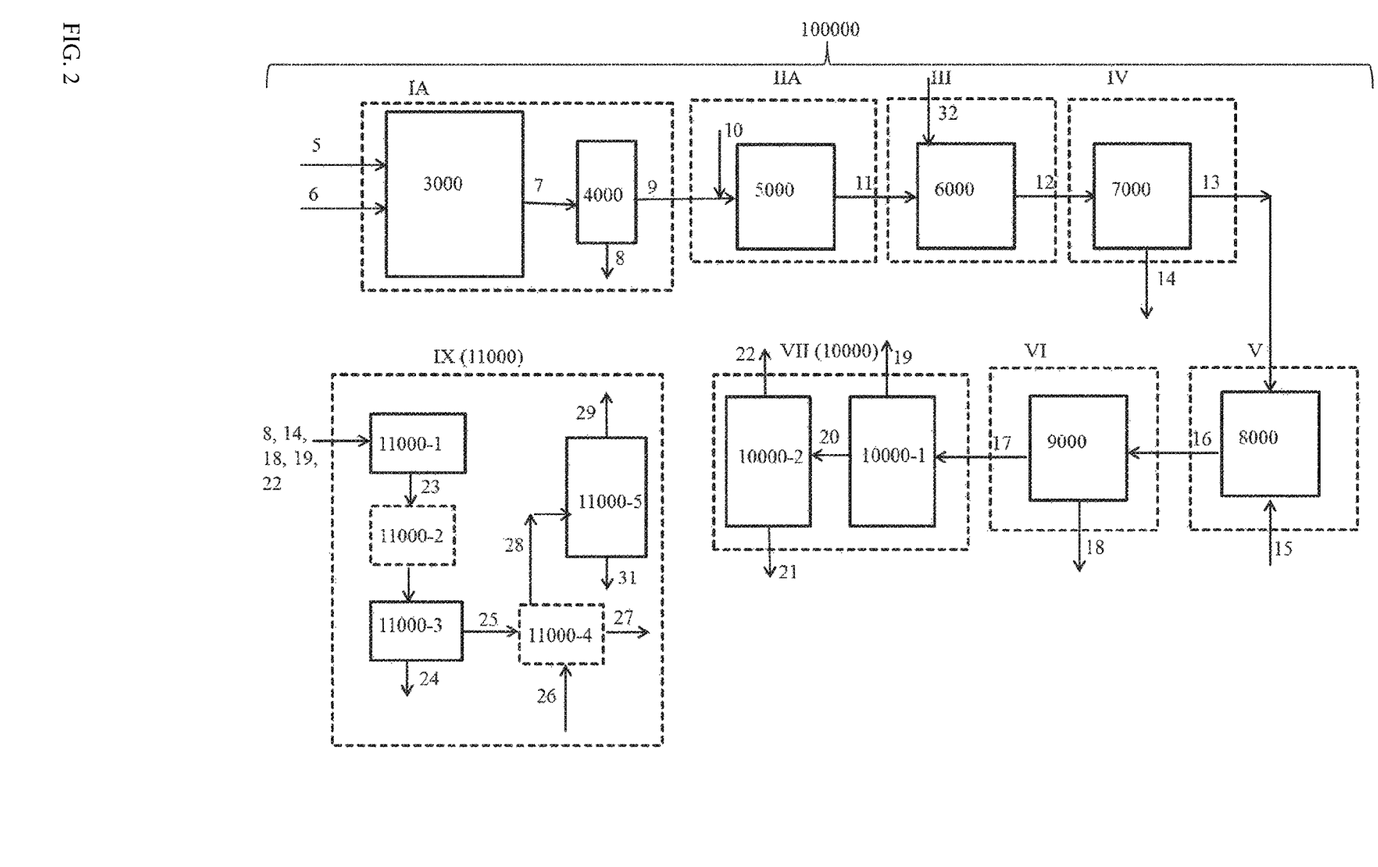
FIG. 2. illustrates an exemplary apparatus configuration of the process stage for preparation of the amine to be phosgenated using the animal process.

The MDA process stage (β) C)) preferably comprises the following steps:

IA) reacting aniline (5) and formaldehyde (6) in a reactor (3000) in the absence of an acidic catalyst to form an animal, followed by separating the reaction mixture obtained into an aqueous phase (8) and an organic phase (9) comprising the animal in a phase separation unit integrated into the reactor or in a separate phase separation apparatus (4000);

IIA) reacting at least a portion of the organic phase comprising the animal which is obtained in step IA) in a reactor (5000) with acid (10), with reaction of the animal to give a mixture (11) of methylene diphenylene diamine and polymethylene polyphenylene polyamine;
—"animal process"—
or IB) reacting aniline (5) and acid (10) in a reactor;

IIB) reacting at least a portion of the reaction mixture obtained in step IB) in a reactor with formaldehyde (6) to give a mixture (11) of methylene diphenylene diamine and polymethylene polyphenylene polyamine;
—"neutralization process"—

III) neutralizing the reaction mixture (11) obtained in step IIA) or IIB) in a reactor (6000);

IV) separating the neutralized reaction mixture (12) obtained in step III) into an organic phase (β) comprising a mixture of methylene diphenylene diamine and polymethylene polyphenylene polyamine and into an aqueous phase (14) in a separation vessel (7000);

V) washing the organic phase (13) with washing liquid (15) in a wash vessel (8000);

VI) separating the mixture (16) obtained in step V) into an organic phase (17) comprising a mixture of methylene diphenylene diamine and polymethylene polyphenylene polyamine and into an aqueous phase (18) in a separation vessel (7000);

VII) distilling the organic phase from step VI) in a distillation apparatus (10000) comprising a first distillation stage (10000-1) for removal of a water- and aniline-containing stream (19) and a second distillation stage (10000-2) for further purification of the process product (20) remaining in the first stage after removal of the water- and aniline-containing stream, with removal of a (moist) aniline-containing stream (22) to obtain a mixture (21) of methylene diphenylene diamine and polymethylene polyphenylene polyamine, with optional use of stripping vapor in the second stage (10000-2) for direct transfer of heat;

VIII) optionally separating methylene diphenylene diamine from the mixture (21) of methylene diphenylene diamine and polymethylene polyphenylene polyamine obtained in step VII).

More preferably, step VIII) is followed by the following:

IX) workup
 of the aqueous phase from step IA) or
 of the aqueous phase from step IV) or
 of the aqueous phase from step VI) or
 of the water- and aniline-containing stream from step VII) or
 of a mixture of two or more of the aforementioned aqueous process products
 in a wastewater workup unit (11000) comprising a wastewater collection vessel (11000-1), optionally a wastewater heater (11000-2), a separation vessel (11000-3), optionally an extraction vessel (11000-4) and a wastewater distillation column (11000-5; e.g. a wastewater stripper);

wherein the heat-consuming operation from step (ii) is selected from the group consisting of:
 the separation of the water- and aniline-containing stream from the organic phase from step VI) in the distillation stage (10000-1),
 the further purification of the process product remaining in the first distillation stage (10000-1) after removal of the water- and aniline-containing stream in the distillation stage (10000-2), where, in the case of use of stripping vapor for direct heat transfer in (10000-2), this stripping vapor comprises the vapor generated in step (i) and preferably consists solely of the vapor generated in step (i),
 if the wastewater heater (11000-2) is present, the heating of the wastewater heater (11000-2), and
 combinations of two or more of the aforementioned operations.

A preferred apparatus configuration of the process stage for preparation of the amine to be phosgenated in this embodiment using the animal process is shown in FIG. 2 (without apparatuses for the optional step VIII)). Single-digit to double-digit reference numerals denote streams of matter having the meaning given above. All apparatuses have been given four- or five-digit reference numerals. The reference numerals mean:

3000: reactor;
4000: separation vessel;
5000: reactor for reaction of the organic phase obtained from 4000 with acid;
6000: reactor for neutralization of the reaction mixture from 5000;
7000: separation vessel for separation of the neutralized reaction mixture from 5000 into an organic phase and an aqueous phase;
8000: wash vessel for washing the organic phase from 7000 with wash liquid;
9000: separation vessel for separation of the mixture from 8000 into an organic phase and an aqueous phase;
10000: distillation unit for distillation of the organic phase from 9000;
 10000-1: first distillation stage ("preliminary evaporator");
 10000-2: second distillation stage ("MDA column");
11000: wastewater workup unit for workup of the aqueous process product from 4000 and/or from 7000 and or from 9000 and or from 10000-1;
 11000-1: wastewater collection vessel to accept the wastewater streams mentioned;
 11000-2: optional waste water heater for heating of the combined wastewater streams (23);
 11000-3: separation vessel for removal of organic, aniline-containing constituents (24) from (23);
 11000-4: optional extraction vessel which may be designed with one or more stages for extraction of the aqueous process product (25) that remains after the removal of organic, aniline-containing constituents (24) from (23) with aniline (26), with removal of an organic phase (27) comprising aniline and MDA;

11000-5: wastewater distillation column for purification of the aqueous process product from 11000-3 or from 11000-4 (25) or (28) to obtain cleaned wastewater (29) and an aniline-containing stream (31).

In one embodiment of the invention, excess energy from the MDI preparation process (process stage of phosgenation), in the form of vapor, specifically in the form of vapor from the vapor generator of the condenser (2310) of the distillation apparatus (2200) (the "solvent column") is thus fed via a pipeline to the MDA process (to the preparation of the amine to be phosgenated), where it is utilized, for example, as stripping vapor in the distillation stage (8000-2) or as heating vapor for the distillation stage (10000-1) ("preliminary evaporator for the MDA column") or as heating vapor for heating of the wastewater heater (10000-2) or as heating vapor for the wastewater distillation column (11000-5; "aniline stripper"). However, it is not absolutely necessary to feed the vapor obtained in the vapor generator of the condenser (2310) completely to the MDA stage; a portion can also be used in some other way.

In a further embodiment of the invention, excess energy from the MDI preparation process (process stage of phosgenation) is used in a process for preparing hydrochloric acid as a further chemical product by absorption of hydrogen chloride in water or dilute (0.1% to 20%, based on mass) hydrochloric acid. The hydrochloric acid thus prepared is used as acid in step (β) C) IIA) or (β) C) IB), wherein the heat-releasing operation from step (i) is the at least partial liquefaction of the gaseous stream (110) in the condenser (2310) and wherein the heat-consuming operation is the direct or indirect heating of the bottom of the absorption column from the process stage for preparation of the hydrochloric acid.

In a further preferred embodiment of the invention relating to the production of aromatic isocyanates, especially the production of TDI, the phosgenation takes place in the gas phase. More particularly, this embodiment relates to a process in which the phosgenation in process stage (α) C) and/or in process stage (β) D) comprises the following:

0) providing gaseous phosgene (3) by evaporating liquid phosgene;

I) evaporating the amine (2) to be phosgenated, reacting the evaporated amine with gaseous phosgene (3) from step 0) in the gas phase, stopping the reaction by contacting with a solvent-containing stream at a temperature below the boiling point of the amine ("quench") and separating the process product obtained into a liquid stream (60) comprising the crude isocyanate and solvent and a gaseous stream (70) comprising phosgene and hydrogen chloride;

II) separating the liquid stream (60) from step I) into a liquid stream (80) comprising solvent and crude isocyanate, and a gaseous stream (90) comprising phosgene and hydrogen chloride in a distillation apparatus (2100);

III) separating the liquid stream (80) into a gaseous stream (110) comprising solvent and a liquid stream (100) comprising crude isocyanate in a distillation apparatus (2200);

IV) separating the gaseous stream (110), after it has been at least partly liquefied in a condenser (2310), into a liquid stream (120) comprising solvent and a gaseous stream (130) comprising phosgene in a distillation apparatus (2300);

V) obtaining a liquid isocyanate stream (140) from the liquid stream (100), giving a gaseous stream (150) comprising secondary components with or without solvents and a mixture of polymeric components ("residue") and monomeric isocyanate (TDI) as stream (143), in a distillation apparatus (2400) preferably designed as a dividing wall column.

TDI in particular is advantageously preparable in process chain (α) by this embodiment of the invention. In this embodiment, the heat-consuming operation from step (ii) is preferably at least one partial step of the evaporation of the liquid phosgene in step 0). Preferably, this evaporation takes place in that liquid phosgene is preheated in a first stage, and heated further and evaporated in a second stage. Particularly the first stage of this two-stage evaporation is configured as the at least one heat-consuming operation in the context of the present invention, meaning that the liquid phosgene is preheated by means of indirect heating by the vapor generated in step (i). Step 0) may, in preferred configurations of the invention, as well as the straight evaporation of the phosgene, also comprise further steps. Thus, it is possible to guide the gaseous phosgene stream obtained at first into a column ("phosgene desorption column") in which impurities such as CO or inert gases are removed, and to use the purified phosgene gas stream in step I).

The vapor used in the evaporation of the liquid phosgene in step 0) preferably comes from the process stage for preparation of the amine to be phosgenated in process stage (α) B), i.e. the TDA preparation in particular. More preferably, the heat-releasing operation from step (i) in this embodiment is the (exothermic) hydrogenation of the aromatic nitro compound (especially dinitrotoluene) to give the aromatic amine (especially TDA), wherein the heat of reaction released is utilized for generation of vapor at a pressure of 1.31 bar$_{(abs.)}$ to 1.91 bar$_{(abs.)}$ and a temperature of 107° C. to 119° C. However, it is also possible to take this vapor from a plant in another process chain, for example the process step of liquid phase phosgenation of MDA to MDI in the MDI process chain.

For the preparation of the isocyanate in the gas phase as well, reference may be made to FIG. 1, although in that case there is no unit (2410) (meaning that stream 100 is guided directly into the distillation apparatus 2400; cf. the conduit shown as a dotted line for stream 100 in FIG. 1), and the distillation apparatus (2400) is preferably configured as a dividing wall column. Purified isocyanate (140), i.e. pure TDI in particular, is withdrawn from the column (2400) as a sidestream, while a mixture of polymeric components ("residue") and monomeric isocyanate (especially TDI) is obtained at the bottom of the column as stream (143). In this embodiment, the removal of polymeric isocyanate fractions is thus integrated into the distillation apparatus (2400) in apparatus terms. Step 0) (evaporation of the phosgene) and the evaporation of the amine are not shown for reasons of drawing simplification. In this embodiment, it is also not obligatory to use phosgene and amine in the form of solutions. It is possible to feed solvent (4) for the first time to the rear portion of the reaction space (1200) in flow direction to stop the reaction ("quench") (likewise not shown in FIG. 1).

So far, specific examples for heat integration within one of the process chains (α) or (β) have been illustrated. However, it is likewise possible to conduct both process chains in the same integrated production system and to undertake the heat integration between them. In this embodiment, the process of the invention accordingly comprises process chain (α) and process chain (β), wherein the at least one heat-releasing operation from step (i) is part of process chain (α) and the at least one heat-consuming operation from step (ii) is part of process chain (β)

or wherein
the at least one heat-releasing operation from step (i) is part of process chain (β) and the at least one heat-consuming operation from step (ii) is part of process chain (α).

A specific configuration of this procedure is shown in example 3.

In all embodiments of the process of the invention, it is preferable
in step (i) to generate the vapor by means of an apparatus for indirect heat transfer which is preferably selected from the group consisting of natural circulation boilers, forced circulation boilers, forced passage boilers, shell and tube heat exchangers, U-tube heat exchangers, double tube coil heat exchangers, plate heat exchangers, tube heat exchangers, spiral heat exchangers and inserted condensers and/or (if heat is not transferred by direct input of vapor)
in step (ii) to provide the amount of heat required for the performance of the heat-consuming operation by means of an apparatus for indirect heat transfer which is preferably selected from the group consisting of natural circulation evaporators, forced circulation evaporators, inserted evaporators, self-circulation evaporators (e.g. the Robert evaporator; see Reinhard Billet: Verdampfung and ihre technischen Anwendungen [Evaporation and Its Industrial Applications], Weinheim, 1981, p. 119 ff.), rising-film evaporators, falling-film evaporators, plate evaporators, helical tube evaporators, thin-film evaporators, short-path evaporators, shell and tube heat exchangers and spiral heat exchangers.

In all embodiments of the process of the invention, it is also preferable, by adjusting
the size of the vapor stream guided from the vapor-releasing point in step (i) to the position of the vapor-consuming operation in step (ii) or
the nominal width of the pipeline used in step (ii) or
the size of the vapor stream guided from the vapor-releasing point in step (i) to the position of the vapor-consuming operation in step (ii) and the nominal width of the pipeline from step (iii),
to bring about a velocity of the vapor of stream in the pipeline, calculated from the quotient of the volume flow rate of the vapor and the cross section of the pipeline, in the range from 10.0 m/s to 40.0 m/s.

This procedure ensures that the process does not become uneconomic owing to excessively low vapor velocities (because, in the case of excessively low vapor velocities, the diameter chosen for the vapor conduit has to be relatively high, which in turn entails elevated expenditure of material and insulation), nor do operational problems or even safety problems occur owing to excessively high vapor velocities (because, in the case of excessively high vapor velocities, erosion can occur at the inner wall of the vapor pipe, up to and including loss of wall material).

The amount of vapor provided by the vapor-releasing site in step (i) may be divided here into multiple component streams, each of which is sent to a different heat-consuming operation. The volume flow rate of the vapor can be easily calculated here from the known mass flow rate of the vapor and the density under the existing pressure and temperature conditions, which can be ascertained by the person skilled in the art in a simple manner from available tabular works. The effect of setting the vapor velocity within the abovementioned range is that excessively large pipeline cross sections on the one hand and excessively high pressure drops and the risk of erosion (in the case of droplet formation in the vapor) on the other hand are avoided.

In all embodiments of the invention, it is further preferable that the pipeline for use in step (ii) has a length of not more than 400 m, preferably of not more than 350 m and more preferably of not more than 300 m, and an internal diameter $d_i$ in the range from 300.0 mm to 1000 mm. The minimum length of the pipeline results from the construction circumstances including safety requirements (for example a due minimum distance from particular plant components) and is otherwise not subject to any restrictions. It is preferable to restrict the length of the pipeline to the minimum ascertained, taking account of the construction circumstances. For every pipeline length chosen, an internal diameter of the pipeline in the range from 300.0 mm to 1000 mm may be used. In general, it will be immediately possible to read off from the standard specification data from pipeline manufacturers whether a particular pipe has an internal diameter within the range specified. In the case of doubt, the internal diameter can be measured in a simple manner. For the determining both of the length and of the internal diameter, the respective value at 20° C. is crucial. If required, pipeline sections can be measured in a hall at a controlled temperature of 20° C. prior to incorporation thereof into an integrated production system. Observing these parameters makes it possible to minimize the pressure drop across the pipeline and heat losses. The optimal combination of length and internal diameter within the above-defined ranges is dependent on the boundary conditions (spatial distance between vapor-releasing and vapor-consuming site, vapor pressure, mass flow rate of the vapor obtained) and can be readily ascertained by the person skilled in the art via routine experiments and/or computer simulations. For further minimization of heat losses, preference is given to isolating the pipeline. This is especially true in the case of pipeline lengths close to the maximum possible in accordance with the invention and/or under particular conditions, such as the construction of an integrated production system at sites with a low annual average temperature. Another possibility in principle is trace heating of the vapor; however, since this would worsen the economic viability of the process, this procedure is generally not the procedure of choice.

The process of the invention and the integrated production system of the invention result in at least the following advantages:
i) there are no costs for the cooling of otherwise unutilized vapor;
ii) in that production plant that uses the residual heat, there is a saving of higher-value forms of energy, for example vapor at of a pressure of 6000 mbar gauge.
iii) the net vapor demand of the overall integrated production system is reduced (reduction in the main vapor generation for the integrated production system).

These advantages i) to iii) may each occur individually or advantageously in combination.

The present invention is to be illustrated hereinafter by means of examples.

EXAMPLES

General Conditions for the Preparation of a Mixture of Methylene Diphenylene Diisocyanate and Polymethylene Polyphenylene Polyisocyanate (Collectively MDI Hereinafter) with Internal Heat Integration of the Vapor obtained in the First Solvent Column—see also FIG. 1

46 t/h of a mixture of methylene diphenylene diamine and polymethylene polyphenylene polyamine (2, collectively MDA hereinafter) at a temperature of 115° C. are mixed with 118.5 t/h of monochlorobenzene (4, MCB) at a temperature of 60° C. as solvent by means of a static mixer (not shown) to give a 30% MDA solution (20). Phosgene is provided by means of a phosgene generator and a phosgene liquefier (both not shown). Thereafter, the phosgene is diluted to a 55% phosgene solution (30) with MCB in a phosgene dissolution tank (1030). 165 tonnes per hour of 55% phosgene solution (30) at a temperature of −3° C. are reacted with 46 tonnes per hour of MDA in the form of the 30% MDA solution (20) at a temperature of 76° C. in an adiabatic reaction, as described in EP 1 873 142 B1. After the two raw material solutions have been mixed in the mixing apparatus (1100), the reaction solution (50) obtained is run at a temperature of 95° C. through a suspension conduit into a heated phosgenation tower (1200). At the top of the phosgenation tower, the absolute pressure is 2.5 bar and the temperature is 105° C. The hydrogen chloride formed in the reaction is removed together with traces of phosgene and MCB as gas stream (70). The liquid reaction mixture (60) is withdrawn from the phosgenation tower and sent to the workup sequence. For this purpose, it is introduced as feed stream into a heated dephosgenation column (2100). At a top temperature of 136° C. and an absolute pressure of 2.5 bar, phosgene is removed overhead together with traces of MCB and hydrogen chloride (90). Phosgene is absorbed in a phosgene absorption column (not shown) and run into the phosgene dissolution tank (1030), and hydrogen chloride is directed into a hydrogen chloride absorber (not shown) and then into a hydrochloric acid tank (not shown) for further use. After removal of hydrogen chloride and excess phosgene from the isocyanate-containing reaction solution, a crude isocyanate solution (80) is obtained, which is discharged from the bottom of the dephosgenation column (2100) and run at a temperature of 175° C. into a first distillation stage (2200), in order to free it of the MCB solvent. The absolute pressure at the top of this solvent distillation column is 800 mbar at a bottom temperature of 155° C. MCB is drawn off overhead in gaseous form (110) at 124° C. and liquefied with a condenser (2310) at 119° C. The condenser (2310) is fed with condensate, obtaining 20 t/h of vapor at a pressure of 1.51 bar$_{(abs.)}$ at a temperature of 112° C. 1 t/h of this vapor is utilized in order to drive traces of MCB out of the hydrochloric acid in the hydrogen chloride absorber (not shown). A further 1 t/h of this vapor is expended for trace heating in the MDI plant. The 18 t/h of this vapor at pressure 1.51 bar$_{(abs.)}$ that still remain are "destroyed" by means of an air cooler, and the remaining condensate is sent to the circuit of the condensate system. The reaction product (100) is discharged from the bottom of the column and freed of residual MCB down to 1% in a second column (not shown). Subsequently, in a countercurrent evaporator, at an absolute pressure of 8 mbar and a bottom temperature of 214° C., the product is freed of secondary components such as phenyl isocyanate and residual MCB. This affords, as bottom product from the second column (not shown), 58 t/h of MDI, which is separated or purified by means of further distillation (2410/2400), giving polymeric fractions 141 (which also contain proportions of monomeric MDI, mMDI) and monomeric fractions 140, both of which are then run into the corresponding MDI product tanks for further use.

General Conditions for the Preparation of Methylene Diphenylene Diamine and Polymethylene Polyphenylene Polyamine (Collectively MDA Hereinafter)—see also FIG. 2

In a continuous reaction process, 76 t/h of input aniline (5) at a temperature of 30° C. (corresponding to 95% by mass of aniline) and 23.3 t/h of 37% aqueous formalin solution (6) at a temperature of 40° C. are mixed and converted to the aminal at 93° C. and an absolute pressure of 1.04 bar in a stirred reaction tank (3000). The reaction mixture (7) leaving the reaction tank is guided into a phase separation apparatus (4000, "animal separator"). After the phase separation to remove the aqueous phase (8), which is guided to a wastewater collection vessel (11000-1), the organic phase (9) is admixed in a mixing nozzle (not shown) with 9.4 t/h of 30% aqueous hydrochloric acid (3) and run into the first rearrangement reactor. The rearrangement reaction is conducted in a reactor cascade (5000) at 50° C. to 130° C. On completion of reaction, the reaction mixture (11) obtained is admixed with 10.7 t/h of 32% sodium hydroxide solution (32) and converted in a stirred neutralization vessel (6000). The temperature is 105° C. and the absolute pressure is 1.04 bar. The neutralized reaction mixture (12) is then separated in a neutralization separator (7000) into an aqueous lower phase (14), which is guided to a wastewater collection vessel (11000-1), and into an organic phase (13). The organic upper phase is directed to the washing operation and washed in a stirred wash vessel (8000) with condensate and/or water from internal water circuits (aniline/water mixture) (15). After removal of the wash water (18) in a wash water separator (9000), the crude MDA (17) thus obtained is pre-evaporated with 8.6 t/h of 6 bar (gauge) vapor in (10000-1) and freed of water and aniline (22) with the aid of 2 t/h of 6 bar (gauge) stripping vapor in the distillation apparatus (10000-2), to obtain 50 t/h of MDA as bottom product (21). The wash water (18) and the condensed top products from the distillation apparatus (10000-1)—stream (19) containing aniline and water—and from the distillation apparatus (10000-2)—stream (22) containing aniline and water—are guided to a wastewater collection vessel (11000-1). The collected wastewater is separated in a separation vessel (11000-3) into an organic phase (24) containing aniline (wet, saturated with water up to the solubility limit), and an aqueous phase (25) containing organic constituents. The aqueous phase (25) is freed of aniline (29) in a wastewater stripper (11000-5) with the aid of 13 t/h of 6 bar (gauge) stripping vapor, before it goes into the final wastewater treatment.

Example 1 (Inventive): Utilization of the Residual Energy from the Heat Integration of the First Solvent Column for the MDI as 1.51 Bar$_{(abs.)}$ Vapor in the MDA Process The preparation of 58 t/h of MDI in continuous mode is conducted as described in the general conditions. The residual heat from the heat integration of the solvent distillation column of the MDI plant is sent as vapor at a pressure of 1.51 bar$_{(abs.)}$ at a temperature of 112° C. through a DN700 pipeline (internal diameter 695.0 mm) into the MDA plant. The pipeline length between the solvent distillation column of the MDI plant and the branch in the MDA plant is 235 m. 8 t/h of this vapor are utilized in the MDA plant for heating in the preliminary evaporation (10000-1) of the input stream to the MDA column (a further 25 m of DN300 pipeline; internal diameter 309.7 mm), a further 2 t/h of this vapor are used as stripping vapor in the MDA column (10000-2) (a further 15 m of pipeline), and the remaining 8 t/h of this vapor are used in the wastewater stripper (11000-5) (a further 40 m of DN300 pipeline). The remaining amount of 4.1 t/h of 1.51 bar$_{(abs.)}$ vapor for the complete replacement of the 7.01 bar$_{(abs.)}$ vapor otherwise required for the operation of the wastewater stripper (11000-5) is supplied from an adjacent aniline plant in the MDI process chain.

Conclusion: The procedure of the invention saves a total of 19.2 t/h of vapor at a pressure of 7.01 bar$_{(abs.)}$ in the MDA plant.

Example 2 (Inventive): Utilization of the Residual Energy from the Heat Integration of the First Solvent Column for the MDI as 1.51 bar$_{(abs.)}$ Vapor in the MDA Process The preparation of 58 t/h of MDI in continuous mode is conducted as described in the general conditions. The first solvent distillation column (2200) is operated with different parameters, giving rise to higher-grade vapor. As described in the general conditions, the crude isocyanate solution is discharged from the bottom of the dephosgenation column (2100) and run into the first distillation stage (2200) at a temperature of 177° C. The absolute pressure at the top of this solvent distillation column is 1.5 bar at a bottom temperature of 155° C. MCB (110) is drawn off overhead in gaseous form at 147° C. and liquefied with a condenser (2310) at 140° C. The condenser (2310) is fed with condensate, obtaining 19.6 t/h of vapor at a pressure of 1.51 bar$_{(abs.)}$ at a temperature of 112° C. 0.8 t/h of this vapor is utilized in order to drive traces of MCB out of the hydrochloric acid in the hydrogen chloride absorber (not shown). A further 0.8 t/h of this vapor is expended for trace heating in the MDI plant. The 18 t/h of this 1.51 bar$_{(abs.)}$ vapor still remaining from the residual heat from the heat integration of the solvent distillation columns of the MDI plant is sent as 1.51 bar$_{(abs.)}$ vapor at a temperature of 112° C. via a distributor pipe conduit into the MDA plant. 2 t/h of this vapor are used as stripping vapor in the MDA column (10000-2), a further 12.1 t/h of this vapor are used in the wastewater stripper (11000-5), and the remaining amounts of vapor are used in a nitrobenzene plant in the MDI process chain.

Conclusion: The procedure of the invention saves 14 t/h of vapor at a pressure of 7.01 bar$_{(abs.)}$ in the MDA plant, and, owing to the higher vapor pressure of the residual heat vapor by comparison with example 1, the pipeline diameter of the heat transfer conduit between the plants is 33% smaller, which means that the capital cost of the pipeline is lower and lower heat losses are also recorded.

Example 3 (Inventive): Utilization of the Residual Energy from the Heat Integration of the First Solvent Column for the MDI as 1.51 bar$_{(abs.)}$ Vapor in the MDA Process The procedure is as in example 2, except that the residual amounts of vapor are not used in a nitrobenzene plant in the MDI process chain as in example 2, but instead in the hydrogen chloride absorption in the TDI plant in an adjacent TDI process chain.

The invention claimed is:

1. A process for preparing m isocyanates in m process chains, in each of which an isocyanate is prepared as end product via at least one intermediate, comprising:
   conducting each of the m process chains in at least 2 production plants, comprising a first production plant designed for preparation of the at least one intermediate and a second production plant designed for preparation of the isocyanate end product, wherein the at least 2 production plants are part of an integrated production system, and
   preparing a total of n chemical products selected from the group consisting of intermediates, catalysts and isocyanate end products in the integrated production system, where n is a natural number in the range from 2 to 40, and where m is a natural number in the range from 1 to n,
   wherein, in the preparation of each of the n chemical products, at least one heat-releasing or heat-consuming operation takes place and, in the process for preparing the m isocyanates, a total of at least one heat-releasing operation and at least one heat-consuming operation takes place,
   wherein
   (i) the heat energy released in a heat-releasing operation in the preparation of one of the chemical products in the first production plant is utilized at least partly for generation of vapor at a pressure of 1.31 bar$_{(abs.)}$ to 1.91 bar$_{(abs.)}$ and a temperature of 107° C. to 119° C.;
   (ii) the vapor generated in (i) is used for performing a heat-consuming operation in the preparation of a chemical product different than the chemical product prepared in step (i), where the preparation of the chemical product different than the chemical product prepared in step (i) takes place in the second production plant, wherein the vapor generated in (i) is guided from the vapor-releasing point in step (i) via a pipeline to the position of the heat-consuming operation in step (ii).

2. The process of claim 1, in which the isocyanate end product is selected from the group consisting of methylene diphenylene diisocyanate, polymethylene polyphenylene polyisocyanate, mixtures of methylene diphenylene diisocyanate and polymethylene polyphenylene polyisocyanate, tolylene diisocyanate, xylylene diisocyanate, pentane 1,5-diisocyanate, hexamethylene diisocyanate, isophorone diisocyanate and naphthyl diisocyanate.

3. The process of claim 1, in which the isocyanate end product is an aromatic isocyanate and in which a first process chain (α) comprises:
   A) nitrating an aromatic hydrocarbon in a first process stage to give an aromatic nitro compound;
   B) hydrogenating the aromatic nitro compound in a second process stage by hydrogenation to give an aromatic amine; and
   C) converting the aromatic amine in a third process stage by phosgenation to give the aromatic isocyanate end product;
and/or
a second process chain (β) comprises:
   A) nitrating an aromatic hydrocarbon in a first process stage to give an aromatic nitro compound;
   B) hydrogenating the aromatic nitro compound in a second process stage to give an aromatic amine;
   C) converting the aromatic amine in a third process stage to another aromatic amine; and
   D) phosgenating the another aromatic amine in a fourth process stage to give the aromatic isocyanate end product.

4. The process of claim 3, in which the phosgenation in process stage (α) C) and/or in process stage (β) D) comprises:

I) reacting the amine to be phosgenated with phosgene in the liquid phase and separating the process product obtained into a liquid stream comprising the crude isocyanate and solvent, and a gaseous stream comprising phosgene and hydrogen chloride;

II) separating the liquid stream from step I) into a liquid stream comprising solvent and crude isocyanate, and a gaseous stream comprising phosgene and hydrogen chloride in a distillation apparatus;

III) separating the liquid stream comprising and crude isocyanate into a gaseous stream comprising solvent and a liquid stream comprising crude isocyanate in a distillation apparatus;

IV) separating the gaseous stream comprising solvent, after it has been at least partly liquefied in a condenser, into a liquid stream comprising solvent and a gaseous stream comprising phosgene in a distillation apparatus;

V) obtaining a liquid isocyanate stream from the liquid stream comprising crude isocyanate, resulting in a gaseous stream comprising secondary components and optionally solvent, in a distillation apparatus, optionally comprising a step V.1) comprising removing polymeric isocyanate fractions in an upstream unit for polymer removal.

5. The process of claim 4, comprising process chain (β), wherein the amine phosgenated in process stage (β) D) is a mixture of methylene diphenylene diamine and polymethylene polyphenylene polyamine, wherein step V.1) is conducted and the isocyanate end product is obtained in two streams and, wherein one stream comprises methylene diphenylene diisocyanate and another stream comprises a mixture of methylene diphenylene diisocyanate and polymethylene polyphenylene polyisocyanate.

6. The process of claim 5, in which the heat-releasing operation from step (i) is the at least partial liquefaction of the gaseous stream comprising solvent in the condenser, and in which the vapor generated by the release of heat is guided into process stage (β) C).

7. The process of claim 6, in which process stage (β) C) comprises:

in a variant A)

IA) reacting aniline and formaldehyde in a first reactor in the absence of an acidic catalyst to form an aminal, followed by separating the reaction mixture obtained into an aqueous phase and an organic phase comprising the aminal in a phase separation unit integrated into the reactor or in a separate phase separation apparatus;

IIA) reacting at least a portion of the organic phase comprising the aminal which is obtained in step IA) in a second reactor with acid, with reaction of the aminal to give a mixture of methylene diphenylene diamine and polymethylene polyphenylene polyamine;

or in a variant B)

IB) reacting aniline and acid in a reactor;

IIB) reacting at least a portion of the reaction mixture obtained in step IB) in a reactor with formaldehyde to give a mixture of methylene diphenylene diamine and polymethylene polyphenylene polyamine;

and in either variant A) or B),

III) neutralizing the reaction mixture obtained in step IIA) or IIB) in a third reactor;

IV) separating the neutralized reaction mixture obtained in step III) into an organic phase comprising a mixture of methylene diphenylene diamine and polymethylene polyphenylene polyamine and into an aqueous phase in a separation vessel;

V) washing the organic phase with washing liquid in a wash vessel;

VI) separating the mixture obtained in step V) into an organic phase comprising a mixture of methylene diphenylene diamine and polymethylene polyphenylene polyamine and into an aqueous phase in the separation vessel;

VII) distilling the organic phase from step VI) in a distillation apparatus comprising a first distillation stage for removal of a water- and aniline-containing stream and a second distillation stage for further purification of the process product remaining in the first stage after removal of the water- and aniline-containing stream to obtain a mixture of methylene diphenylene diamine and polymethylene polyphenylene polyamine, with optional use of stripping vapor in the second stage for direct transfer of heat; and VIII) optionally separating methylene diphenylene diamine from the mixture of methylene diphenylene diamine and polymethylene polyphenylene polyamine obtained in step VII).

8. The process of claim 7, in which process stage (β) C) further comprises:

IX) workup of the aqueous phase from step IA) or of the aqueous phase from step IV) or of the aqueous phase from step VI) or of the water- and aniline-containing stream from step VII) or of a mixture of two or more of the aforementioned aqueous process products in a wastewater workup unit comprising a wastewater collection vessel, optionally a wastewater heater, a separation vessel, optionally an extraction vessel and a wastewater distillation column;

wherein the heat-consuming operation from step (ii) is selected from the group consisting of:

separation of the water- and aniline-containing stream from the organic phase from step VI) in the first distillation stage, further purification of the process product remaining in the first distillation stage after removal of the water- and aniline-containing stream in the second distillation stage, where, in the case of use of stripping vapor for direct heat transfer in the second distillation stage, this stripping vapor comprises the vapor generated in step (i), heating of the wastewater heater if present, and a combination of two or more thereof.

9. The process of claim 7, further comprising a process stage of preparing hydrochloric acid as a further chemical product, wherein the hydrochloric acid is prepared by absorption of hydrogen chloride in water or 0.1% to 20% hydrochloric acid in an absorption column, wherein the hydrochloric acid thus prepared is used as acid in step (β) C) IIA) or (β) C) IB), wherein the heat-consuming operation comprises the direct or indirect heating of the bottom of the absorption column from the process stage for preparation of hydrochloric acid.

10. The process of claim 3, in which the phosgenation in process stage (α) C) and/or in process stage (β) D) comprises:

0) providing gaseous phosgene by evaporating liquid phosgene;
I) evaporating the amine to be phosgenated, reacting the evaporated amine with gaseous phosgene from step 0) in the gas phase, stopping the reaction by contacting with a solvent-containing stream at a temperature below the boiling point of the amine and separating the process product obtained into a liquid stream comprising the crude isocyanate and solvent and a gaseous stream comprising phosgene and hydrogen chloride;
II) separating the liquid stream from step I) into a liquid stream comprising solvent and crude isocyanate, and a gaseous stream comprising phosgene and hydrogen chloride in a distillation apparatus;
III) separating the liquid stream comprising solvent and crude isocyanate into a gaseous stream comprising solvent and a liquid stream comprising crude isocyanate in a distillation apparatus;
IV) separating the gaseous stream comprising solvent, after it has been at least partly liquefied in a condenser, into a liquid stream comprising solvent and a gaseous stream comprising phosgene in a distillation apparatus; and
V) obtaining a liquid isocyanate stream from the liquid stream comprising crude isocyanate, giving a gaseous stream comprising secondary components with or without solvents and a mixture of polymeric components and monomeric isocyanate as stream, in a distillation apparatus.

11. The process of claim 10, comprising process chain (α), in which the heat-consuming operation from step (ii) is at least one partial step of the evaporation of liquid phosgene in step 0) and in which the heat-releasing operation from step (i) originates from process stage (α) B).

12. The process of claim 3, comprising process chain (α) and process chain (β), in which the at least one heat-releasing operation from step (i) is part of process chain (α) and the at least one heat-consuming operation from step (ii) is part of process chain (β)

or in which the at least one heat-releasing operation from step (i) is part of process chain (β) and the at least one heat-consuming operation from step (ii) is part of process chain (α).

13. The process of claim 1, in which in step (i) the vapor is generated by means of an apparatus for indirect heat transfer which selected from the group consisting of a natural circulation boiler, a forced circulation boiler, a forced passage boiler, a shell and tube heat exchanger, a U-tube heat exchanger, a double tube coil heat exchanger, a plate heat exchanger, a tube heat exchanger, a spiral heat exchanger and an inserted condensers, or in step (ii) the amount of heat required for the performance of the heat-consuming operation is provided by means of an apparatus for indirect heat transfer which is selected from the group consisting of a natural circulation evaporator, a forced circulation evaporator, an inserted evaporator, a self-circulation evaporator, a, rising-film evaporator, a falling-film evaporator, a plate evaporator, a helical tube evaporator, a thin-film evaporator, a short-path evaporator, a shell and tube heat exchangers, and a spiral heat exchanger, or in step (i) the vapor is generated by means of an apparatus for indirect heat transfer which is selected from the group consisting of a natural circulation boiler, a forced circulation boiler, a forced passage boiler, a shell and tube heat exchanger, a U-tube heat exchanger, a double tube coil heat exchanger, a plate heat exchanger, a tube heat exchanger, a spiral heat exchanger and an inserted condenser, and in step (ii) the amount of heat required for the performance of the heat-consuming operation is provided by means of an apparatus for indirect heat transfer which is selected from the group consisting of a natural circulation evaporator, a forced circulation evaporator, an inserted evaporator, a self-circulation evaporator, a rising-film evaporator, a falling-film evaporator, a plate evaporator, a helical tube evaporator, a thin-film evaporator, a short-path evaporator, a shell and tube heat exchanger, and a spiral heat exchanger.

14. The process of claim 1, comprising bringing about a velocity of the vapor stream in the pipeline, calculated from the quotient of the volume flow rate of the vapor and the cross section of the pipeline, of from 10.0 m/s to 40.0 m/s by adjusting the size of the vapor stream guided from the vapor-releasing point in step (i) to the position of the heat-consuming operation in step (ii) or the nominal width of the pipeline used in step (ii) or the size of the vapor stream guided from the vapor-releasing point in step (i) to the position of the heat-consuming operation in step (ii) and the nominal width of the pipeline from step (iii).

15. The process of claim 1, in which the pipeline has a length of not more than 400 m and an internal diameter $d_i$ in the range from 300.0 mm to 1000 mm.

* * * * *